US011285331B2

(12) United States Patent
Whittington et al.

(10) Patent No.: US 11,285,331 B2
(45) Date of Patent: Mar. 29, 2022

(54) IMPLANTABLE MEDICAL DEVICE COMPRISING AN ANCHORING DEVICE

(71) Applicant: BIOTRONIK SE & CO. KG, Berlin (DE)

(72) Inventors: R. Hollis Whittington, Portland, OR (US); Dirk Muessig, West Linn, OR (US); Brian M. Taff, Portland, OR (US); Nicholas Devich, Tualatin, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 16/990,383

(22) Filed: Aug. 11, 2020

(65) Prior Publication Data
US 2021/0069519 A1 Mar. 11, 2021

Related U.S. Application Data

(60) Provisional application No. 62/897,407, filed on Sep. 9, 2019.

(30) Foreign Application Priority Data

Oct. 22, 2019 (EP) .................................. 19204500

(51) Int. Cl.
A61N 1/375 (2006.01)
(52) U.S. Cl.
CPC ....... A61N 1/37518 (2017.08); A61N 1/3756 (2013.01); A61N 1/37512 (2017.08)

(58) Field of Classification Search
CPC ............ A61N 1/37518; A61N 1/37512; A61N 1/3756; A61N 1/37205; A61N 1/0573; A61N 1/375
See application file for complete search history.

(56) References Cited

U.S. PATENT DOCUMENTS

| 9,119,959 | B2 * | 9/2015 | Rys ..................... A61N 1/37518 |
| 9,526,891 | B2 | 12/2016 | Eggen et al. |
| 9,844,659 | B2 | 12/2017 | Grubac et al. |
| 2009/0082827 | A1 | 3/2009 | Kveen et al. |
| 2012/0172892 | A1 * | 7/2012 | Grubac ................ A61N 1/0573 606/129 |

(Continued)

FOREIGN PATENT DOCUMENTS

WO 2012102836 A1 8/2012

Primary Examiner — Eugene T Wu
(74) Attorney, Agent, or Firm — Laurence A. Greenberg; Werner H. Stemer; Ralph E. Locher

(57) ABSTRACT

An implantable medical device includes a housing having a proximal end and a distal end. The implantable medical device is placeable on cardiac tissue in the region of the distal end. An anchoring device is fixedly attached to the housing in the region of the distal end. The anchoring device includes at least one anchoring member. The at least one anchoring member includes a first end and a second end opposite the first end. The second end is disposed on the housing. The at least one anchoring member longitudinally extends between the first end and the second end along an axis of extension and is formed by a flat strip which is twisted by a twist angle about the axis of extension between the first end and the second end. A method for manufacturing an implantable medical device is also provided.

14 Claims, 6 Drawing Sheets

(56) References Cited

U.S. PATENT DOCUMENTS

| | | |
|---|---|---|
| 2013/0085350 A1 | 4/2013 | Schugt et al. |
| 2017/0209689 A1 | 7/2017 | Chen et al. |
| 2019/0054288 A1 | 2/2019 | Grubac et al. |
| 2019/0083779 A1 | 3/2019 | Yang et al. |

* cited by examiner

IMPLANTABLE MEDICAL DEVICE COMPRISING AN ANCHORING DEVICE

CROSS-REFERENCE TO RELATED APPLICATION

This application claims the benefit, under 35 U.S.C. § 119 of U.S. Provisional Patent Application No. 62/897,407, filed Sep. 9, 2019 and of European Patent Application EP 19204500, filed Oct. 22, 2019; the prior application are herewith incorporated by reference in their entirety.

BACKGROUND OF THE INVENTION

Field of the Invention

The present disclosure generally relates to an implantable medical device and a method for manufacturing an implantable medical device.

An implantable medical device of this kind may, for example, be a leadless pacemaker for implantation into the human heart, for example, in the right ventricle or the right atrium of the human heart.

In recent years, leadless pacemakers have received increasing attention. Leadless pacemakers, in contrast to pacemakers implanted subcutaneously (using leads extending transvenously into the heart), avoid leads in that the pacemaker device itself is implanted into the heart. The pacemaker has the shape of a generally cylindrical capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

When placing an implantable medical device such as a leadless pacemaker device for example in the human heart, one challenge lies in constructing an anchoring device allowing a fixation of the implantable medical device for example on cardiac tissue in such a way that the implantable medical device is securely received and held on cardiac tissue. For that purpose, the anchoring device on the one hand must provide for a secure fastening of the implantable medical device on the cardiac tissue, but on the other hand must avoid damaging cardiac tissue and structures within the cardiac tissue.

A typical anchoring device includes anchoring members in the shape of tines which, when placing the implantable medical device on cardiac tissue, pierce the cardiac tissue and in this way provide for an anchoring of the implantable medical device on the cardiac tissue. In order to place the implantable medical device on cardiac tissue, the implantable medical device for example is received within a sheathing device of a delivery catheter, the delivery catheter being used to access the human heart and to deliver the implantable medical device towards a location of interest by removing the sheathing device and by in this way placing the implantable medical device on cardiac tissue at the location of interest. Upon delivering the implantable medical device from the sheathing device, the anchoring members engage with cardiac tissue to provide for a fastening of the implantable medical device on the cardiac tissue.

U.S. Pat. No. 9,844,659 B2 describes an assembly of an implantable medical device including an anchoring device having a set of active fixation tines. The active fixation tines in the set are deployable from a spring-loaded position in which distal ends of the fixation tines point away from the implantable medical device to a hooked position in which the active fixation tines bend back towards the implantable medical device.

U.S. Pat. No. 9,526,891 discloses an implantable pacemaker system including a housing having a proximal end and a distal end, a configuration of anchoring members being placed on the distal end of the housing for providing for a fastening of the implantable pacemaker system on cardiac tissue.

Generally, when placing an implantable medical device such as a leadless pacemaker device at a location of interest for example on cardiac tissue, it is to be made sure that the implantable medical device is sufficiently anchored by the anchoring device on tissue in the vicinity of the location of interest. In this case, if the anchoring device includes multiple anchoring members for example in the shape of tines, it is to be observed whether all anchoring members are in engagement with tissue in such a way that the anchoring members together provide for a secure fastening of the implantable medical device on the tissue.

In order to assess engagement of the anchoring members of the anchoring device with tissue, a so-called tug test is performed during the implantation procedure of the implantable medical device. During the tug test a defined force is applied to the medical device by a delivery system used for implanting the medical device and being linked to the medical device for example by a snare or another form of a tether. During such a force application within the tug test, the anchoring members are visualized using for example an x-ray fluoroscopy technique, wherein the shape of the anchoring members are assessed in real time in order to monitor whether the anchoring members during the application of the force are straightening (in which case they are assumed to be engaged in tissue) or retain their shape (in which case they are assumed to be not engaged with tissue).

Hence, in order to access a correct and sufficient anchoring, it is beneficial to visualize the anchoring members, which may not be easily possible because generally anchoring members for example in the shape of tines have small dimensions. In addition, the visibility of an anchoring member also depends on a view plane and view direction of the visualization technique.

BRIEF SUMMARY OF THE INVENTION

It is accordingly an object of the invention to provide an implantable medical device and a method for manufacturing an implantable medical device, which overcome the hereinafore-mentioned disadvantages of the heretofore-known devices and methods of this general type and which allow for a reliable and secure fastening of an implantable medical device at a location of interest, for example in the human heart, and for an easy monitoring in particular during initial implantation for confirming a sufficient anchoring.

With the foregoing and other objects in view there is provided, in accordance with the invention, an implantable medical device, comprising a housing having a proximal end and a distal end, the implantable medical device being placeable on cardiac tissue in the region of the distal end. The implantable medical device furthermore includes an anchoring device fixedly attached to the housing in the region of the distal end, the anchoring device including at least one anchoring member. The at least one anchoring member includes a first end and a second end opposite the first end, the second end being disposed on the housing, wherein the at least one anchoring member longitudinally extends in between the first end and the second end along an axis of extension and is formed by a flat strip which is twisted by a twist angle about the axis of extension in between the first end and the second end.

The implantable medical device includes a housing and an anchoring device disposed on the housing. The anchoring device includes one or multiple anchoring members, for example in the shape of tines protruding from the housing in such a way that the anchoring members may engage with tissue when placing the implantable medical device at a location of interest for example in the human heart, for example in a ventricle or atrium of the heart.

The implantable medical device may in particular be a leadless pacemaker device providing for an electrical stimulation within the human heart. The leadless pacemaker device does not include leads, but is immediately implanted at the location of interest at which a stimulation action shall be performed. In this case, an electrode configuration may be placed on the housing of the leadless pacemaker device in such a way that, upon implantation, an electrode at the distal end of the housing comes to engage with tissue and contacts tissue for injecting stimulation energy into the tissue for example for providing a pacing action.

Since the implantable medical device may be constructed to remain at a location of interest for a prolonged period of time, it is to be made sure that the anchoring device provides for a reliable fastening of the implantable medical device at the location of interest. In order to assess the correct engagement of the anchoring members of the anchoring device with tissue at the location of interest, in this case, during a so-called tug test in the course of the implantation procedure a force is applied to the implantable medical device for example using a delivery system (such as a delivery catheter) and the positioning of the anchoring members on the tissue is visualized using for example an x-ray fluoroscopy technique.

In order to improve the visibility of one or multiple anchoring members of the anchoring device, in this case, an anchoring member is formed to longitudinally extend in between a first end (which is spaced apart from the housing and hence is free) and a second end (at which the anchoring member adjoins the housing). The anchoring member is formed as a flat strip having for example a generally rectangular cross section, the flat strip being twisted by a twist angle about a longitudinal axis of extension in between the first end and the second end.

The anchoring member may be curved, in such a way that the longitudinal axis of extension may be curved, in particular within a two-dimensional plane of extension associated with the anchoring member.

Generally, an anchoring member formed by a flat strip has a cross-sectional shape which does not include a rotational symmetry, but has a width substantially larger than its thickness when viewed in a cross-sectional plane. In this case, the visibility of the anchoring member depends on the orientation of a view plane or respectively a view direction with respect to the position and orientation of the anchoring member. If a (non-twisted) anchoring member for example bends in the coronal plane and is visualized in an anterior-posterior view, the anchoring member may appear thin and may hardly be visible, since the visibility of the anchoring member in the view plane is due only to the cross-sectional material thickness of the anchoring member.

In order to address this and to improve visibility, it is proposed in this case to introduce one or multiple twists about the longitudinal axis of extension. Each twist may involve a twisting by a twist angle of for example 90°, in such a way that by using the twist the orientation of the flat strip forming the anchoring member varies about the axis of extension. Since hence the orientation of the anchoring member changes along the length of the anchoring member along the axis of extension, visibility in a view plane may be increased, since one portion of the anchoring member may appear thin, but another, twisted portion may appear at an increased strength as it is visualized across its width.

In one aspect, the flat strip forming the at least one anchoring member may be twisted about the axis of extension by an angle of 90° or more. The anchoring member may include one or multiple twists, each twist being formed by a twisting of the flat strip by a twist angle of for example 90° or more.

In one example, one or multiple twists defined by a twist angle of 90° are present.

In another example, one or multiple twists defined by a twist angle in between 90° and 180° are present.

In yet another example, one or multiple twists defined by a twist angle less than 90°, for example 45° or 60°, are present.

In one aspect, the flat strip forming the at least one anchoring member is twisted continuously over the length of the at least one anchoring member defined by the first end and the second end. The flat strip forming the anchoring member hence is twisted progressively in between the first end and the second end, in such a way that the full twist angle is obtained in between the first end and the second end. Hence, in this embodiment, the twisting is not confined to a particular (short) twist region of the anchoring member, but takes place continuously and progressively over the entire length of the anchoring member.

In another aspect, the flat strip forming the at least one anchoring member is twisted within at least one twist region confined by a twist length substantially shorter than the length of the at least one anchoring member defined by the first end and the second end. Hence, the twisting is confined to a short region along the length of the anchoring member, but the flat strip forming the anchoring member is not twisted outside of a particular twist region.

For example, each twist region may be adjoined by a flat section of the flat strip forming the anchoring member, the flat section not being twisted about the axis of extension. The anchoring member in this way may for example be made up from multiple flat sections interlinked by twisted regions, the flat sections hence being oriented at different angles with respect to the axis of orientation in such a way that different sections of the anchoring member may be visualized differently within a visualization technique, such as an x-ray fluoroscopy technique, when assessing a correct engagement of the anchoring device on tissue during implantation of the implantable medical device.

In one embodiment, the flat strip forming the at least one anchoring member, in a cross-sectional plane perpendicular to the axis of extension, has a rectangular shape. The flat strip hence does not include a rotational symmetry, but has a width substantially larger than its thickness, when viewed in a cross-sectional plane perpendicular to the axis of extension. By twisting the flat strip at one or multiple locations along the length of the anchoring member, the orientation of the flat strip forming the anchoring member is altered along the length of the anchoring member, in such a way that different portions of the anchoring member may be visualized differently when applying a suitable visualization technique.

The flat strip forming the at least one anchoring member may have a uniform width and thickness along the length of the anchoring member. In another embodiment, however, the width and/or the thickness of the flat strip forming the at least one anchoring member may vary across the length of the anchoring member, the flat strip for example including at least one widened portion having a spatial extension larger than a width or a thickness, when measured in a cross-sectional plane perpendicular to the axis of extension, of another portion of the flat strip adjoining the widened portion. Hence, a widened portion of the flat strip may be adjoined by a narrow portion, wherein multiple widened portions may alternate with multiple narrow portions.

In one embodiment, the at least one anchoring member includes a tip section in the vicinity of the first end, wherein the tip section forms a widened portion having a spatial extension larger than a width or thickness, when measured in a cross-sectional plane perpendicular to the axis of extension, of a portion of the flat strip adjoining the widened portion of the tip section. The widened portion may in particular have a spherical shape in such a way that the anchoring member at its tip section diverts from the general shape of the flat strip forming the anchoring member in portions other than the tip section. Such a widened portion at the tip section may increase visibility of the anchoring member in particular in the region of the tip section when using a suitable visualization technique such as an x-ray fluoroscopy technique, in such a way that according to the visualization of the tip section an engagement of the anchoring member with tissue may reliably be assessed during a tug test within the implantation procedure.

In one embodiment, the at least one anchoring member includes a connection section extending in between the tip section and the housing, wherein the tip section adjoins the connection section by forming a kink. A twist in this case may be introduced in the region of the kink, in such a way that the tip section includes a different orientation about the axis of extension with respect to a portion of the connection section adjoining the tip section. By forming a kink in between the connection section and the tip section it may be achieved that the anchoring member may beneficially engage with tissue when placing the implantable medical device at a location of interest, in such a way that the anchoring member may suitably pierce the tissue and provide for a connection to the tissue. By introducing a twist in between the tip section and the connection section, a distinction in the visualization of the tip section and the connection section may be achieved, in such a way that within the visualization a relative position of the tip section with respect to the connection section may reliably be asserted.

In another aspect, the at least one anchoring member may be made of an alloy including a radiopaque material and/or may be coated with a radiopaque material. In this way, visualization of the at least one anchoring member may be further improved, since the visibility of the material of the anchoring member as such within a suitable visualization technique, such as an x-ray fluoroscopy technique, is improved.

For example, a high atomic number material such as tungsten, gold or another metal material could be included in the alloy forming the anchoring member, for example a nitinol alloy, i.e. a metal alloy of nickel and titanium.

In another example, a coating for example formed by a plating using a high atomic number material such as tungsten, gold or another metal material may be applied to the outside of the material of the at least one anchoring member.

In yet another example, a chemical coating including a material such as iodine or another heavy element is applied to the outside of the at least one anchoring member. The coating material can for example be embedded in a polymer.

In yet another example, a chemical coating to be applied to at least one anchoring member can be biodegradable so that the coating vanishes after some time of resting within tissue. Since an improved visibility of the at least one anchoring member is of particular importance during implantation of the implantable medical device, by using such a biodegradable coating the visualization may be improved during implantation, but once the material of the coating has degraded, a standard visibility of a medical anchoring member may be sufficient for a continued monitoring for example using an x-ray technique.

The anchoring device may include a multiplicity of anchoring members, for example two, three, four or more anchoring members.

The at least one anchoring member or the anchoring device as a whole may for example be made from an elastic metal material, in particular a nickel titanium alloy, also denoted as nitinol (potentially with adding a radiopaque material).

In one embodiment, the anchoring device includes multiple anchoring members interconnected for example by a ring element for fixing the anchoring device to the housing of the implantable medical device. The anchoring members in this case are fixed to the ring element, for example by forming the anchoring members integrally with the ring element. The ring element provides for a fixation of the anchoring device on the housing of the implantable medical device in such a way that the anchoring members are held at the distal end of the housing of the implantable medical device.

With the objects of the invention in view, there is furthermore provided a method for manufacturing an implantable medical device, which comprises providing a housing having a proximal end and a distal end, the implantable medical device being placeable on cardiac tissue in the region of the distal end; and providing an anchoring device to be fixedly attached to the housing in the region of the distal end, wherein the step of providing the anchoring device includes forming at least one anchoring member including a first end and a second end opposite the first end and to be disposed on the housing, and the at least one anchoring member is formed by a flat strip in such a way that the at least one anchoring member longitudinal extends in between the first end and the second end along the axis of extension and is twisted by a twist angle about the axis of extension in between the first end and the second end.

The advantages and advantageous embodiments described above for the implantable medical device equally apply also to the method of manufacturing, in such a way that it shall be referred to the above in this respect.

With the objects of the invention in view, there is concomitantly provided an implantable medical device, which comprises a housing having a proximal end and a distal end, the implantable medical device being placeable on cardiac tissue in the region of the distal end; and an anchoring device fixedly attached to the housing in the region of the distal end, the anchoring device including at least one anchoring member; wherein the at least one anchoring member includes a first end and a second end opposite the first end, the second end being disposed on the housing, the at least one anchoring member longitudinally extends in between the first end and the second end along an axis of extension and includes a tip section in the vicinity of the first end, and the tip section forms a spherical portion having a spatial extension larger than at least one of a width or thickness, when measured in a cross-sectional plane perpendicular to the axis of extension, of a portion of the at least one anchoring member adjoining the spherical portion.

Such a widened, spherical portion at the tip section may increase visibility of the anchoring member in particular in the region of the tip section when using a suitable visualization technique such as an x-ray fluoroscopy technique, so that according to the visualization of the tip section, an engagement of the anchoring member with tissue may reliably be assessed during a tug test within the implantation procedure.

Other features which are considered as characteristic for the invention are set forth in the appended claims.

Although the invention is illustrated and described herein as embodied in an implantable medical device and a method for manufacturing an implantable medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
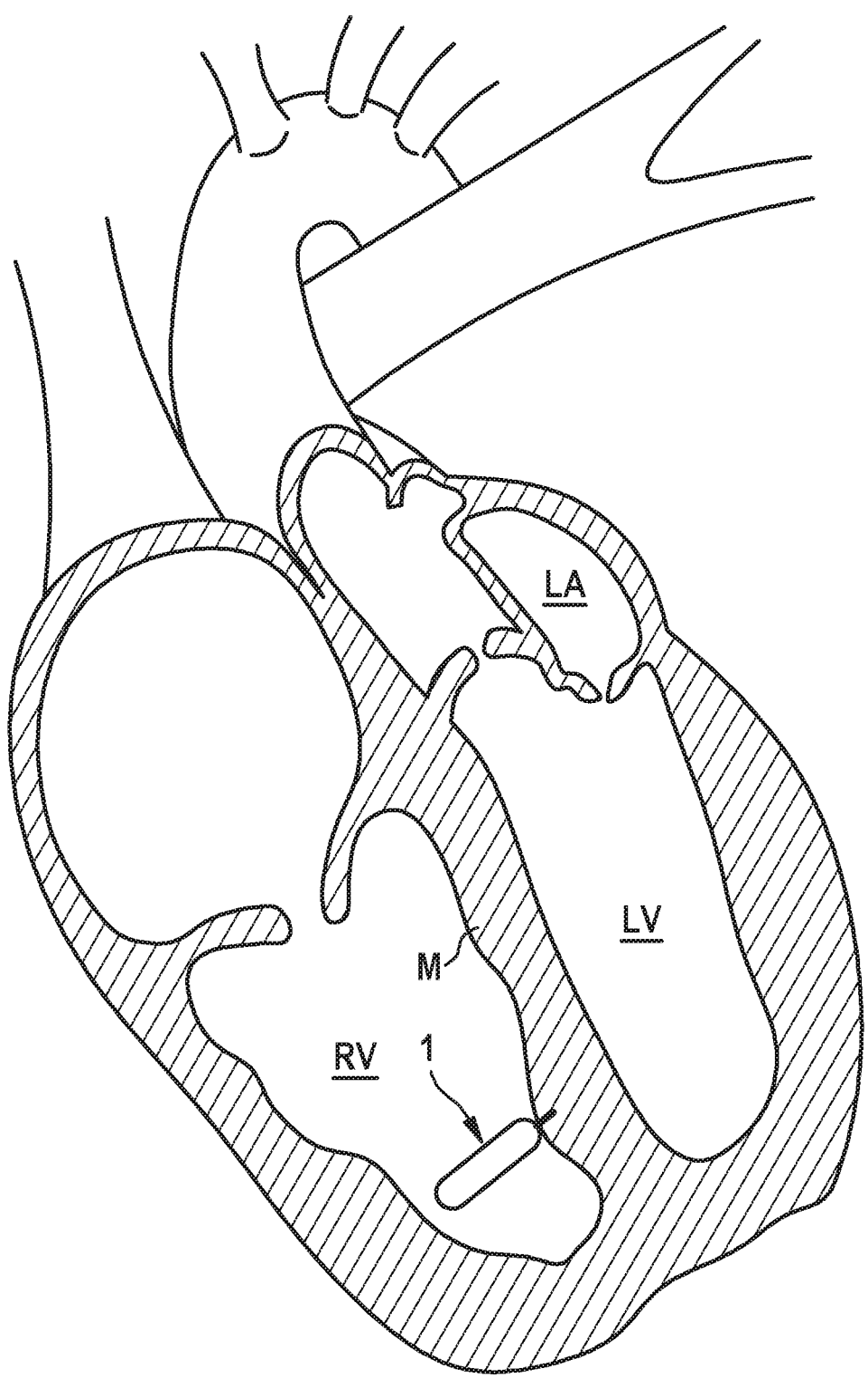
FIG. 1 is a diagrammatic, cross-sectional view of the human heart.

Subsequently, embodiments shall be described in detail with reference to the drawings. In the drawings, like reference numerals designate like structural elements.

It is to be noted that the embodiments are not limiting for the instant disclosure, but merely represent illustrative examples.

Referring now to the figures of the drawings in detail and first, particularly, to FIG. 1 thereof, there is seen a diagrammatic drawing of a human heart including a right atrium RA, a right ventricle RV, a left atrium LA and a left ventricle LV. An implantable medical device 1 is implanted into the right ventricle RV. The implantable medical device 1 for example has the shape of a leadless pacemaker device for providing a pacing of the heart's activity at the right ventricle RV.

For implantation, the implantable medical device 1 is placed in the right ventricle RV by using a delivery system and is delivered from the delivery system in such a way that it comes to rest on myocardial tissue M and is fastened to the myocardial tissue M.

Figure 2:
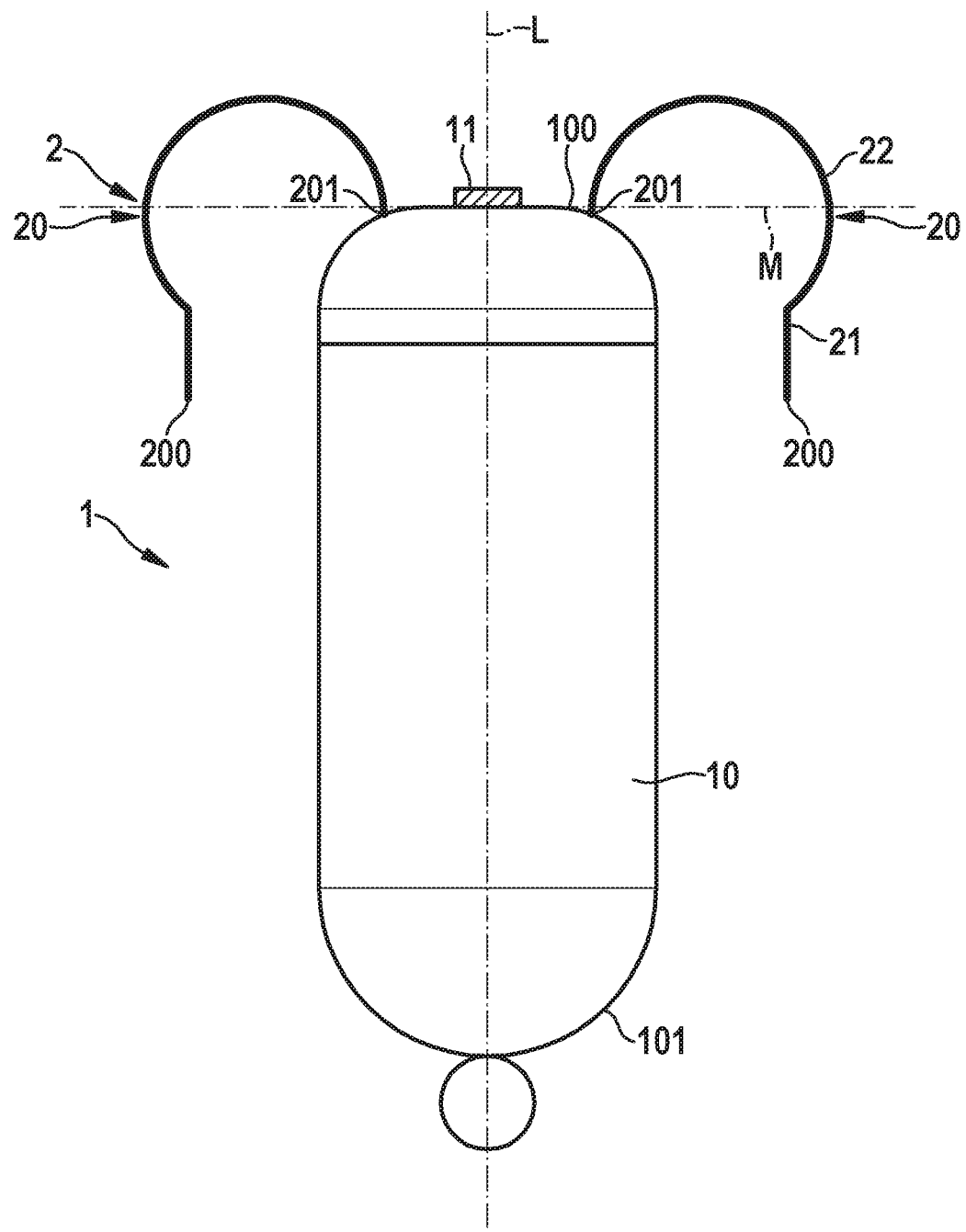
FIG. 2 is an elevational view of an implantable medical device in the shape of a leadless pacemaker device, the implantable medical device having a housing and an anchoring device disposed thereon.

FIG. 2 shows, in a diagrammatic drawing, an example of an implantable medical device 1 in the shape of a leadless pacemaker device, the implantable medical device 1 having a housing 10 forming a proximal end 101 and a distal end 100. The implantable medical device 1 is configured to be placed on myocardial tissue M by its distal end 100. Herein, an electrode device 11, which is placed on the distal end 100, potentially together with other electrodes of the implantable medical device 1, serves to provide for a pacing action in order to stimulate cardiac activity in a defined manner.

During implantation the implantable medical device 1 is to be placed on myocardial tissue M and is to be fastened to the myocardial tissue M. In order to support this fastening, the implantable medical device 1 includes an anchoring device 2 having a multiplicity of anchoring members 20 in the shape of elastically deformable tines. The anchoring members 20 extend from the housing 10 of the implantable medical device 1 at the distal end 100 to engage with myocardial tissue M for (stably) affixing the implantable medical device 1 to the myocardial tissue M.

The anchoring members 20 are fixedly disposed on the distal end 100 of the housing 10 of the implantable medical device 1. In a relaxed state, the anchoring members 20 assume a preshaped configuration, as shown in FIG. 2, which is constructed in such a way that the anchoring members 20 may penetrate through myocardial tissue M in order to form hook-like connections in between the implantable medical device 1 and the myocardial tissue M. Each anchoring member 20 forms a tip section 21 and a connection section 22 extending in between the tip section 21 and the housing 10, the tip section 21 forming a free end of the respective anchoring member 20. In an implanted state, as diagrammatically shown in FIG. 2, the tip section 21 may be placed outside of myocardial tissue M.

Whereas each anchoring member 20 at its tip section 21—in the shown example—is substantially formed straight, the connection section 22 of each anchoring member 20 has a substantially curved shape in order to form a loop through myocardial tissue M for fastening the implantable medical device 1 on the myocardial tissue M.

Each anchoring member 20 herein generally has the same shape, wherein it also is conceivable that different anchoring members 20 of the anchoring device 2 have different shapes.

During implantation, the implantable medical device 1 is placed on tissue at a location of interest at which the implantable medical device 1 is to be fastened within a patient. Herein, it is to be made sure that the anchoring members 20 of the anchoring device 2 engage with the tissue in such a way that the anchoring members 20 contribute to fastening the implantable medical device 1 to the tissue.

For this reason, the correct piercing of tissue by the anchoring members 20 of the anchoring device 2 must be assessed during implantation. For this, within an implantation procedure in which the implantable medical device 1 is introduced towards a location of interest for example in the ventricle of the patient's heart using a delivery system such as a delivery catheter including a sheathing device, a so-called tug test is performed during which a defined pulling force is applied to the proximal end 101 of the housing 10 of the implantable medical device 1 by using the delivery system in order to test whether the implantable medical device 1 is held on the tissue on which it is placed by the anchoring members 20 engaging with the tissue. During such a tug test, the anchoring members 20 are visualized by using for example a suitable x-ray fluoroscopy technique, in such a way that by using the visualization the position and the shape of the anchoring members 20 can be monitored and evaluated to conclude whether the anchoring members 20 provide for a correct and sufficient anchoring of the implantable medical device 1 to the tissue.

In particular, by using the visualization during the tug test it may be assessed whether the anchoring members 20 are deformed under the application of a force. If an anchoring member 20 is straightened when applying a pulling force to the implantable medical device 1, it can be assumed that the particular anchoring member 20 correctly and sufficiently engages with tissue. If, however, an anchoring member 20 retains its shape and does not deform under the application of force, it can be assumed that the particular anchoring member 20 is not engaged with tissue, hence potentially bearing the risk that no sufficient anchoring of the implantable medical device 1 on tissue is achieved.

Visualization however may not be easy, due to the tiny shape of the anchoring members 20 and their material strength. In addition, visualization depends on the orientation of a view plane within a particular visualization technique.

In order to improve the visibility of an anchoring member 20 within a particular visualization technique, it herein is proposed to form the anchoring member 20 in such a way that it is made sure that at least a portion of the anchoring member 20 is reliably visible within a view plane largely independent of a view direction.

Figure 3:
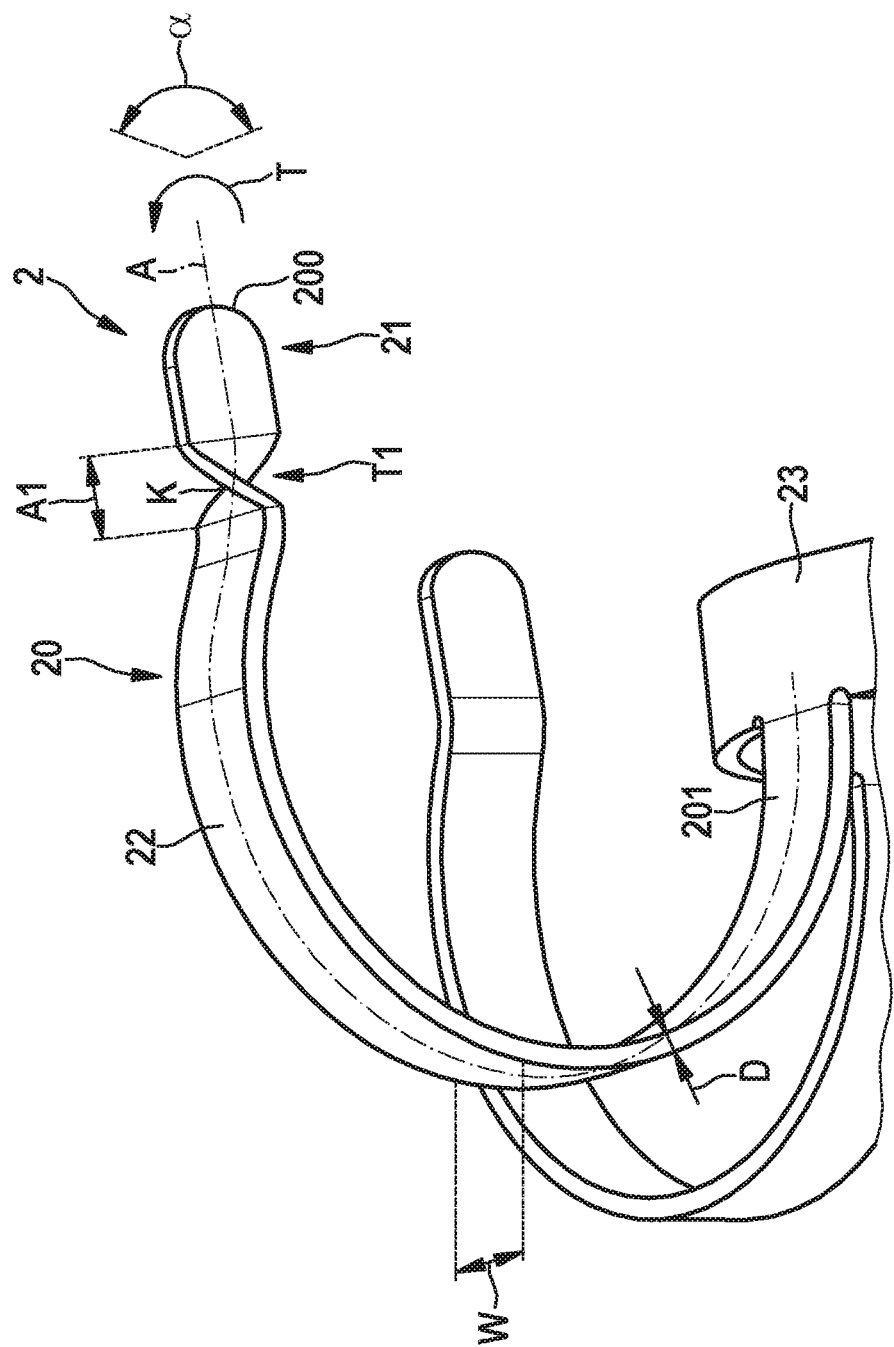
FIG. 3 is a perspective view of an anchoring member of an anchoring device for anchoring an implantable medical device to tissue.

For this purpose, in an embodiment as illustrated in FIG. 3, the anchoring member 20 includes a twist within a twist region T1 in between a tip section 21 and a connection section 22 of the anchoring member 20. The twist provides, in the shown embodiment, for a 90° change of orientation in between the sections 21, 22 of the anchoring member 20.

In the example of FIG. 3, the anchoring member 20 is connected to a ring element 23, with the ring element 23 serving to interconnect multiple anchoring members 20 of the anchoring device 2. Each anchoring member 20 herein longitudinally extends in between an end 201 at which the anchoring member 20 adjoins the ring element 23 and an end 200 which is spaced apart from the ring element 23 and represents a free end of the anchoring member 20 at which the tip section 21 is formed.

The anchoring member 20 herein longitudinally extends about an axis of extension A, the axis of extension A following the curved shape of the anchoring member 20 and representing a neutral axis of the anchoring member 20. The anchoring member 20 is formed from a flat strip having a width W substantially larger than a thickness D, when measured in a cross-sectional plane perpendicular to the axis of extension A, as is visible from FIG. 3.

As a twist by a twist angle α of 90° in a twist direction T is introduced in between the connection section 22 and the tip section 21 within the twist region T1, the rotational orientation of the anchoring member 20 with respect to the axis of extension A changes in between the connection section 22 and the tip section 21. In this way it can be made sure that in a particular view direction at least one of the sections 21, 22 of the anchoring member 20 can be visualized across the width W of the flat strip forming the anchoring member 20 when using for example an x-ray fluoroscopy technique, in such a way that an improved visibility of the anchoring member 20 can be achieved.

If the anchoring member 20 for example bends in a coronal plane (in such a way that the anchoring member 20 fully extends, with its curved shape, within the coronal plane) the connection section 22 in an anterior-posterior view direction is visualized only across its material thickness D and hence appears only as a thin line. The tip section 21, however, due to the 90° twisting with respect to the connection section 22 is visualized across the width W and hence is strongly visible in the anterior-posterior view direction, in such a way that at least the position and orientation of the tip section 21 can be easily monitored.

The tip section 21, in the embodiment of FIG. 3, adjoins the connection section 22 by forming a kink K. The kink K and the twist region T1 herein, in the example of FIG. 3, coincide.

In the example of FIG. 3 the twisting is confined to a rather short twist region T1 having a twist length A1 which is short with respect to the overall length of the anchoring member 20. Hence, a rather abrupt change in orientation in between the connection section 22 and the tip section 21 is obtained.

Figure 4:
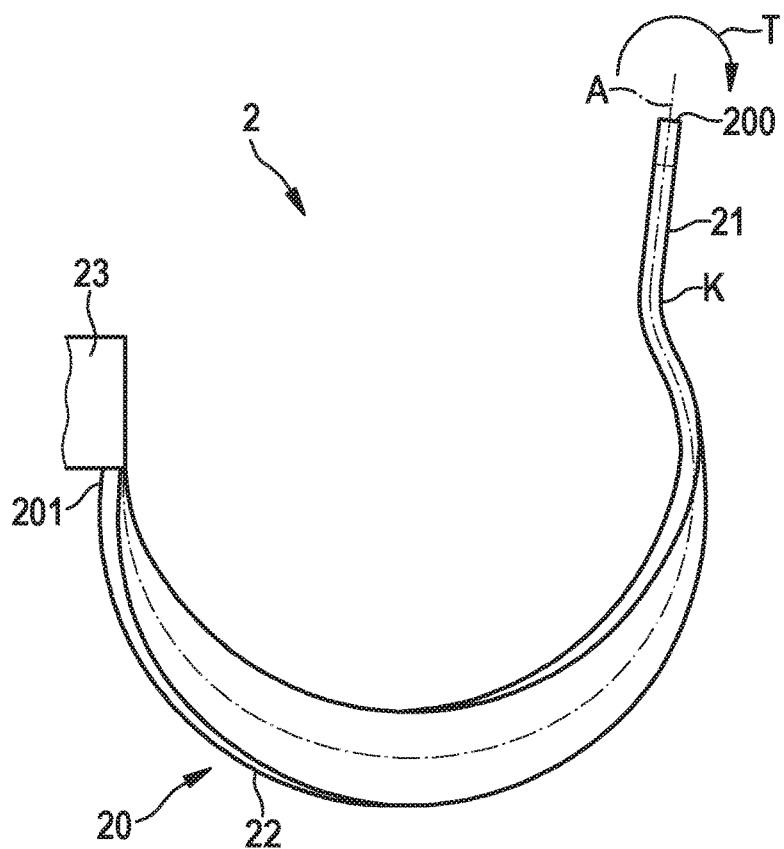
FIG. 4 is a perspective view of another embodiment of an anchoring member of an anchoring device.

In an embodiment shown in FIG. 4, a twist is introduced in an anchoring member 20, the twist being formed by a continuous, progressive twisting of the anchoring member 20 over the entire length of the anchoring member 20 between its end 201 adjoining the ring element 23 and the end 200 at the tip section 21.

In the embodiment of FIG. 4 the anchoring member 20 is twisted in a twist direction T over an overall twist angle of 180°. The ends 200, 201 of the anchoring member 20 hence are oriented along parallel planes.

Figure 5:
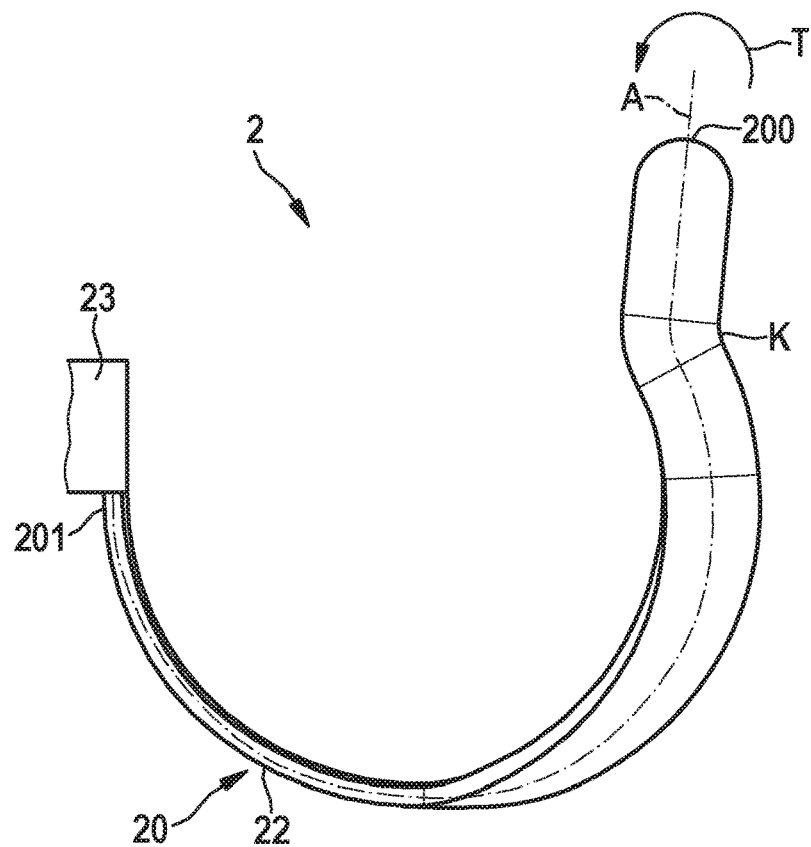
FIG. 5 is a perspective view of yet another embodiment of an anchoring member of an anchoring device.

In contrast, in the embodiment of FIG. 5 the anchoring member 20 is twisted progressively over its overall length between the ends 200, 201 by a twist angle of 90°, in such a way that the anchoring member 20 at its ends 200, 201 extends along perpendicular planes.

In the examples of both FIG. 4 and FIG. 5 the tip section 21 forms a kink K together with the connection section 22.

Figure 6:
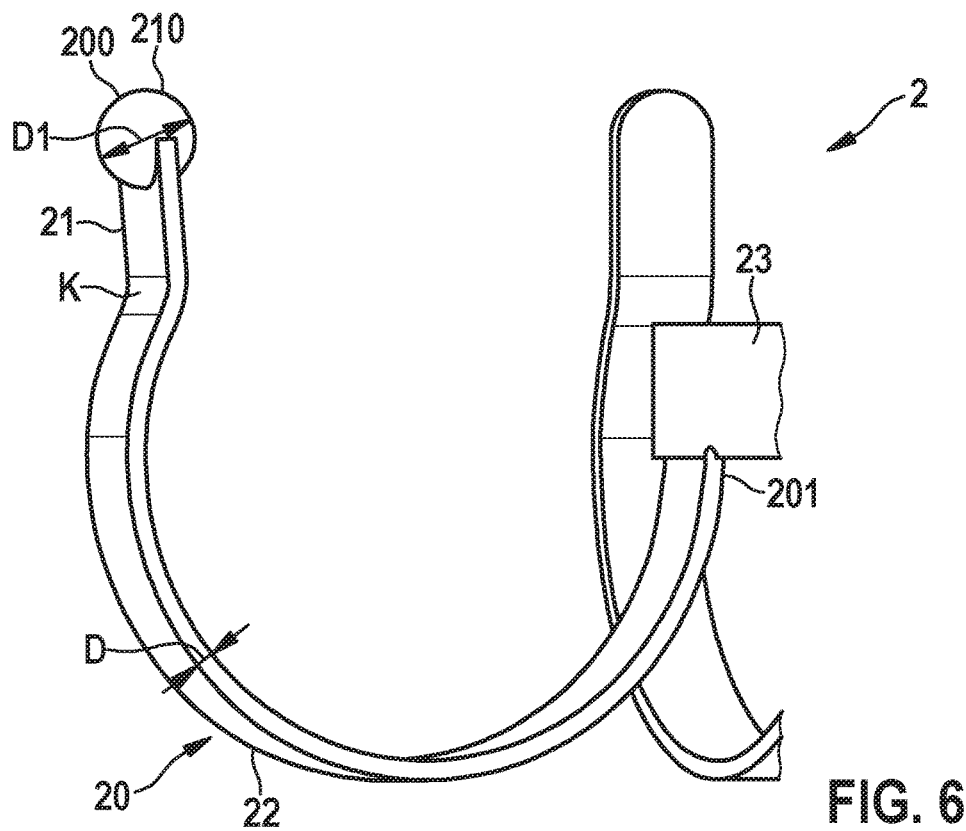
FIG. 6 is a perspective view of yet another embodiment of an anchoring member of an anchoring device.

The visibility of an anchoring member 20 can, in addition or alternatively to introducing a twist into the anchoring member 20, be increased by including a portion on the anchoring member 20 having widened dimensions. Referring now to FIG. 6, in one embodiment a widened portion 210 having a spherical shape may be formed on the tip section 21 at the end 200, the widened portion 210 having in particular a diameter D1 which provides for an increase with respect to the material thickness D of the flat strip forming the anchoring member 20. Through the use of such widened portion 210, hence, an improved visibility in particular in the region of the tip section 21 may be obtained independently of a particular view direction.

The shape of the widened portion 210 is not limited to a spherical shape. Rather, the widened portion 210 may alternatively have for example the shape of a paddle and may provide for a widening of the dimension not only along the thickness direction of the anchoring member 20, but additionally or alternatively along the width direction of the anchoring member 20.

Figure 7:
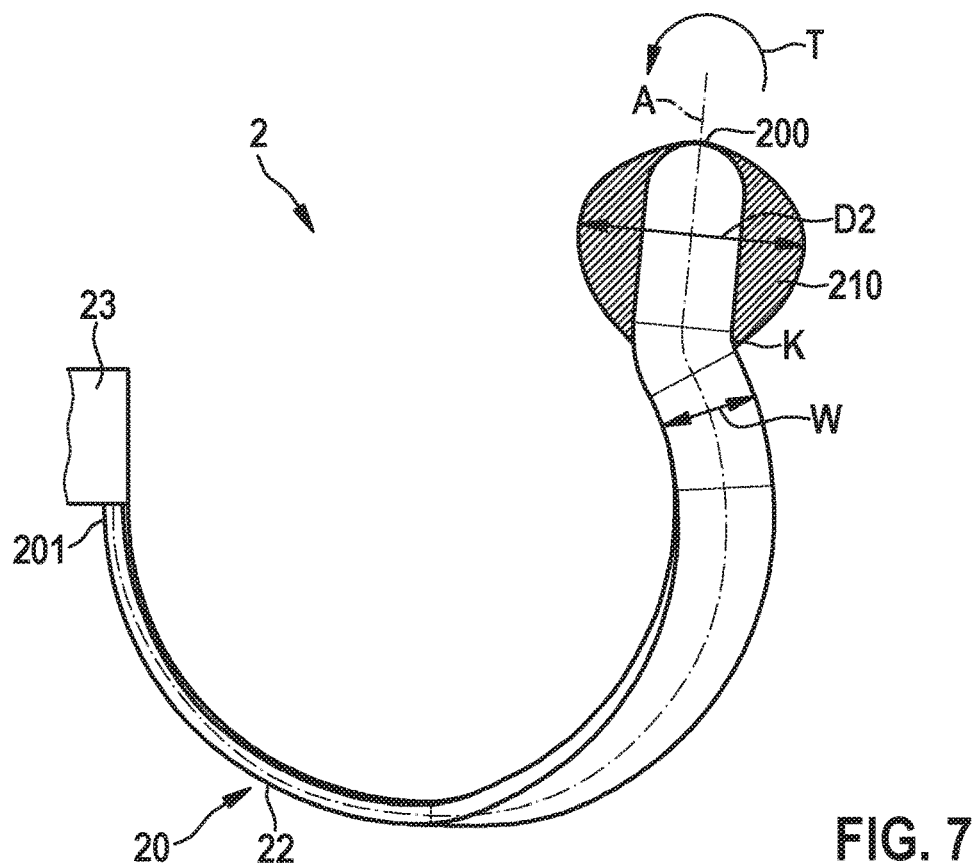
FIG. 7 is a perspective view of yet another embodiment of an anchoring member of an anchoring device.

Referring now to FIG. 7, in another example a widened portion 210 at the tip section 21 may have a paddle shape providing for a widening along the width direction, the widened portion 210 having a width D2 larger than the width W of the flat strip forming the anchoring member 20.

In the example of FIG. 7, the widened portion 210 is formed on an anchoring member 20 being twisted by a twist angle of 90° in between its ends 200, 201, similarly to the example of FIG. 5.

Figure 8:
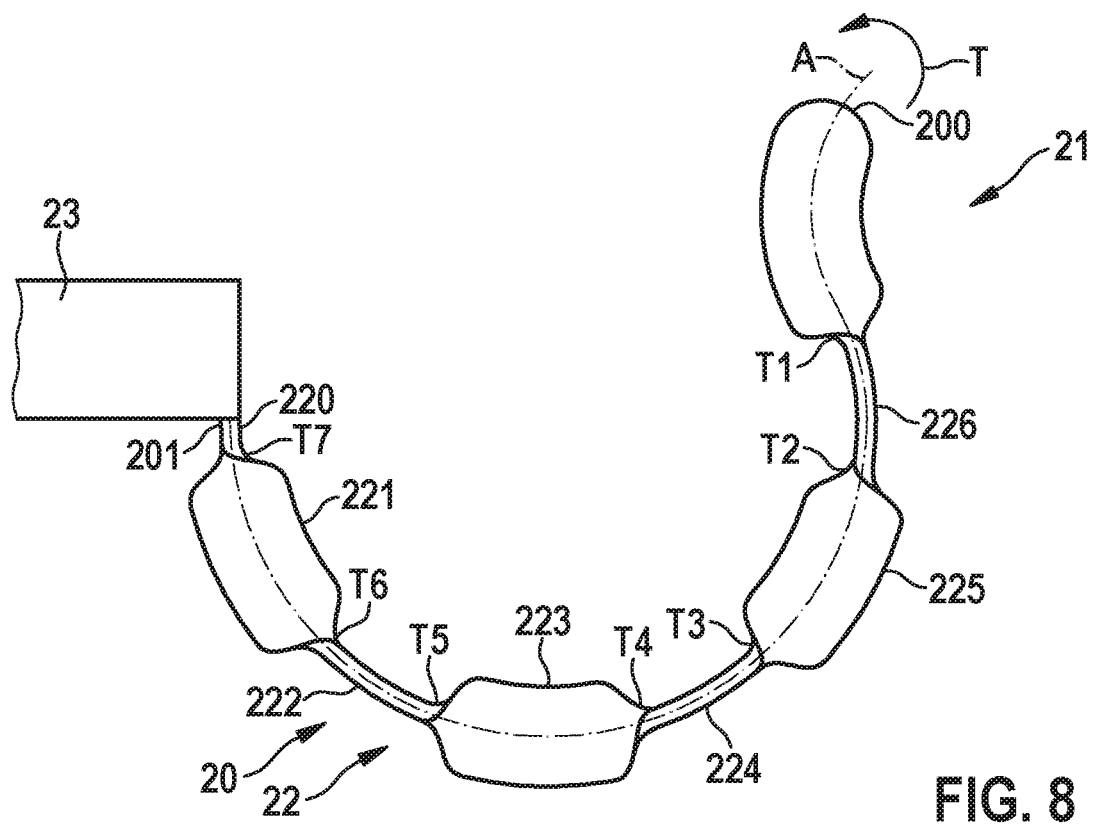
FIG. 8 is a plan view of yet another embodiment of an anchoring member of an anchoring device.

Referring now to FIG. 8, multiple twists can be introduced in an anchoring member 20. In this example, flat sections 220-226, 21 (i.e., sections not having a twist) are interlinked by twists and are oriented at twist angles of for example 90° about the axis of extension A with respect to each other. Each flat section 220-226, 21 herein is twisted with respect to a neighbouring flat section 220-226, 21 within a twist region T1-T7, similarly to that shown in FIG. 3 for the twist region T1 in between the tip section 21 and the connection section 22.

In all of the examples described above, the twisting may generally take place about 90° or about any other angle smaller or larger than 90°. In the example of FIG. 4, for example, a twisting by 180° is introduced.

A twisting by an angle smaller than 90°, for example by 60°, may for example be introduced in between neighboring flat sections 220-226, 21 of the example of FIG. 8.

Figure 9:
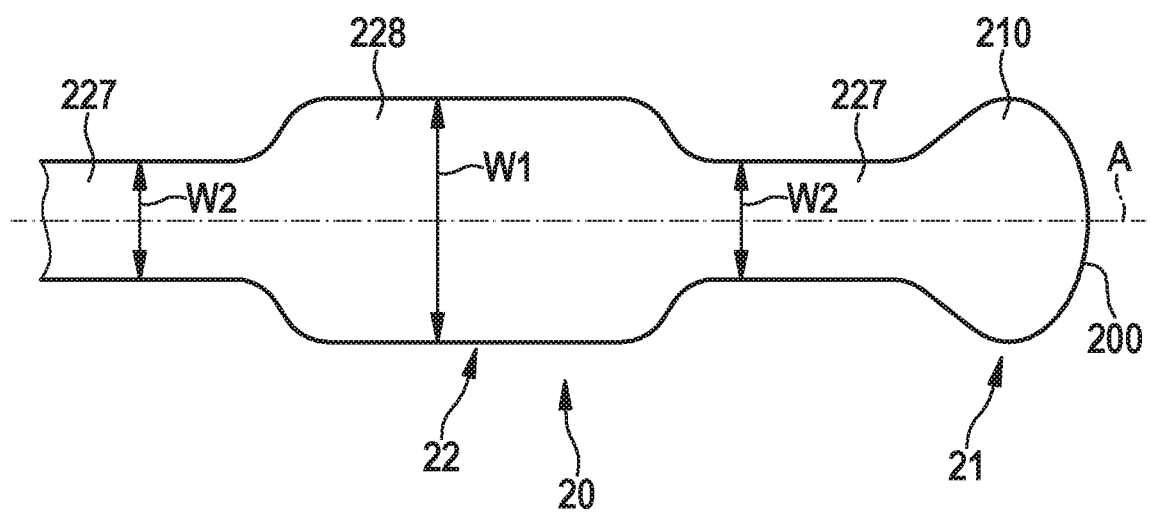
FIG. 9 is a plan view of yet another embodiment of an anchoring member of an anchoring device.

The anchoring member 20 may be formed by a flat strip having a uniform width W, as illustrated for example in the embodiment of FIGS. 3 to 5. However, in another embodiment, it is conceivable that the width W of the flat strip may vary over the length of the anchoring member 20. This is illustrated in FIG. 9, in which the anchoring member 20 is for example formed by widened portions 228 and narrowed portions 227 alternating along the length of the anchoring member 20 along the axis of extension A. A widened portion 228 herein may have a width W1 larger than a width W2 of an adjoining narrowed portion 227, as is visible from FIG. 9.

Also, in the example of FIG. 9, shown herein, a twist may be introduced in the anchoring member 20 about the axis of extension A.

In all of the embodiments described above, the anchoring members 20 of the anchoring device 2 may all have the same shape, or may have a different shape. For example, some of the anchoring members 20 may have a twist, whereas other anchoring members 20 of the anchoring device 2 may not have a twist, as is shown for example in the example of FIG. 3.

In order to improve visibility within a suitable visualization technique, such as an x-ray fluoroscopy technique, in all of the embodiments described above a radiopaque material may be applied to the material of the anchoring members 20. For example, the anchoring members 20 may be made of an alloy including a high atomic number material such as tungsten, gold, or another metal. The anchoring members 20 hence may be made of for example a nickel titanium alloy (nitinol) included with a radiopaque material such as tungsten or gold.

In another embodiment, the anchoring members 20 may be coated with a radiopaque material, for example by applying a plating of a tungsten or gold material.

In yet another embodiment, a chemical coating including a material such as iodine or another heavy element is applied to the outside of the anchoring members, the coating material for example being embedded in a polymer material.

Such a chemical coating can be longer-lasting or can be biodegradable, such that after implantation the biodegradable chemical coating degrades and disappears.

In particular, the implantable medical device may be configured to act as a leadless pacemaker device, although the implantable medical device may also be constructed to provide a different function. The implantable medical device may be configured to be implanted into the right ventricle of the human heart or into another location of, e.g., the human heart or another body part.

The following is a summary list of reference numerals and the corresponding structure used in the above description of the invention:

1 Leadless pacemaker device
10 Housing
100 Distal end
101 Proximal end
11 Electrode
2 Anchoring device
20 Anchoring member
200, 201 End
21 Tip section
210 Widened section
22 Connection section
220-226 Flat sections
227 Narrow portion
228 Widened portion
23 Ring element
α Twist angle
A Axis of extension
A1 Twist length
D Thickness
D1, D2 Diameter
K Kink
L Longitudinal axis
LA Left atrium
LV Left ventricle
M Intra-cardiac tissue (myocardium)
RA Right atrium
RV Right ventricle
T Twist direction
T1-T7 Twist region
W, W1, W2 Width

The invention claimed is:

1. An implantable medical device, comprising:
a housing having a proximal end and a distal end, said housing configured to be placed on cardiac tissue in a region of said distal end; and
an anchoring device fixedly attached to said housing in said region of said distal end, said anchoring device including at least one anchoring member;
said at least one anchoring member including a first end and a second end disposed opposite to said first end, said second end being disposed on said housing;
said at least one anchoring member being longitudinally extended between said first end and said second end along an axis of extension and said at least one anchoring member being formed by a flat strip twisted by a twist angle about said axis of extension between said first end and said second end.

2. The implantable medical device according to claim 1, wherein said twist angle, about which said flat strip forming said at least one anchoring member is twisted about said axis of extension, is at least 90°.

3. The implantable medical device according to claim 1, wherein said at least one anchoring member has a length defined by said first end and said second end, and said flat strip forming said at least one anchoring member is twisted continuously over said length of said at least one anchoring member.

4. The implantable medical device according to claim 1, wherein said at least one anchoring member has a length defined by said first end and said second end, and said flat strip forming said at least one anchoring member is twisted within at least one twist region confined by a twist length substantially shorter than said length of said at least one anchoring member.

5. The implantable medical device according to claim 4, wherein said flat strip forming said at least one anchoring member has a flat section neighboring said at least one twist region, and said flat section is not twisted about said axis of extension.

6. The implantable medical device according to claim 1, wherein said flat strip forming said at least one anchoring member has a rectangular shape in a cross-sectional plane perpendicular to said axis of extension.

7. The implantable medical device according to claim 1, wherein:
    said flat strip forming said at least one anchoring member includes at least one widened portion and a further portion adjoining said widened portion and having a width and a thickness; and
    said at least one widened portion has a spatial extension being larger than at least one of said width or said thickness of said further portion as measured in a cross-sectional plane perpendicular to said axis of extension.

8. The implantable medical device according to claim 1, wherein:
    said at least one anchoring member includes a tip section in a vicinity of said first end;
    said tip section forming a widened portion and a portion of said flat strip adjoining said widened portion and having a width or thickness;
    said widened portion having a spatial extension being larger than at least one of said width or said thickness of said portion of said flat strip adjoining said widened portion as measured in a cross-sectional plane perpendicular to said axis of extension.

9. The implantable medical device according to claim 8, wherein said widened portion of said tip section has a spherical shape.

10. The implantable medical device according to claim 8, wherein said at least one anchoring member includes a connection section extending between said tip section and said housing, said tip section adjoining said connection section by forming a kink.

11. The implantable medical device according to claim 10, wherein said flat strip forming said at least one anchoring member is twisted about said axis of extension in a region of said kink.

12. The implantable medical device according to claim 1, wherein said at least one anchoring member is at least one of made of an alloy including a radiopaque material or coated with a radiopaque material.

13. The implantable medical device according to claim 1, wherein said at least one anchoring member is coated with a biodegradable radiopaque material.

14. A method for manufacturing an implantable medical device, the method comprising:
    providing a housing having a proximal end and a distal end and configuring the housing to be placed on cardiac tissue in a region of the distal end;
    providing an anchoring device to be fixedly attached to the housing in the region of the distal end;
    forming the anchoring device by providing at least one anchoring member having a first end and a second end disposed opposite to the first end and configured to be disposed on the housing; and
    forming the at least one anchoring member from a flat strip, extending the at least one anchoring member longitudinally between the first end and the second end along an axis of extension and twisting the at least one anchoring member through a twist angle about the axis of extension between the first end and the second end.

\* \* \* \* \*